(12) United States Patent
Fröse et al.

(10) Patent No.: US 8,760,652 B2
(45) Date of Patent: Jun. 24, 2014

(54) APERTURE SYSTEM FOR MULTI-ANGLE LIGHT SCATTERING DETECTORS

(71) Applicant: Postnova Analytics GmbH, Landsberg (DE)

(72) Inventors: Dietheim Fröse, Berlin (DE); Roland Welz, Schongau (DE)

(73) Assignee: Postnova Analytics GmbH, Landsberg (DE)

( * ) Notice: Subject to any disclaimer, the term of this patent is extended or adjusted under 35 U.S.C. 154(b) by 1 day.

(21) Appl. No.: 13/654,747

(22) Filed: Oct. 18, 2012

(65) Prior Publication Data

US 2013/0100433 A1 Apr. 25, 2013

(30) Foreign Application Priority Data

Oct. 18, 2011 (EP) .................................... 11185620

(51) Int. Cl.
*G01N 21/00* (2006.01)

(52) U.S. Cl.
USPC .......................................... 356/338; 356/343

(58) Field of Classification Search
None
See application file for complete search history.

(56) References Cited

U.S. PATENT DOCUMENTS

| | | | | |
|---|---|---|---|---|
| 3,508,830 | A * | 4/1970 | Hecht et al. ................... | 356/338 |
| 3,835,315 | A * | 9/1974 | Gravitt, Jr. .................... | 250/574 |
| 4,160,914 | A * | 7/1979 | Wynn ............................ | 250/574 |
| 4,188,121 | A * | 2/1980 | Hirleman et al. ............. | 356/336 |
| 4,616,927 | A | 10/1986 | Phillips et al. | |
| 4,907,884 | A * | 3/1990 | Philips et al. ................. | 356/336 |
| 5,485,013 | A * | 1/1996 | Cummins ...................... | 250/574 |
| 5,654,797 | A * | 8/1997 | Moreau et al. ................ | 356/336 |
| 6,052,184 | A | 4/2000 | Reed | |
| 7,538,874 | B2 * | 5/2009 | Palumbo ....................... | 356/338 |
| 2007/0195324 | A1 | 8/2007 | Adams et al. | |
| 2009/0091757 | A1 | 4/2009 | Yang | |
| 2011/0242535 | A1 | 10/2011 | Frose | |

FOREIGN PATENT DOCUMENTS

| | | | |
|---|---|---|---|
| DE | 3813718 | A1 * | 11/1989 |
| EP | 0182618 | A2 | 5/1986 |
| EP | 0626064 | | 8/1998 |
| WO | 93/16372 | A1 | 8/1993 |
| WO | 98/52013 | A1 | 11/1998 |
| WO | 2004/106916 | A1 | 12/2004 |
| WO | 2010/036736 | A2 | 1/2010 |
| WO | 2010/057490 | A1 | 5/2010 |

* cited by examiner

*Primary Examiner* — Gordon J Stock, Jr.
(74) *Attorney, Agent, or Firm* — Hodgson Russ LLP (57) ABSTRACT

An apparatus for measuring the light scattering properties of a sample in a liquid medium, wherein the liquid medium with the sample is illuminated by a laser beam in a measuring cell transversely to the direction of filling the liquid medium in the measuring cell or transversely to the flow direction of the liquid medium within the measuring cell, comprising a laser, a cylindrical measuring cell, a first inner aperture system, a second outer aperture system and at least two detectors, wherein the detectors are arranged outside of the second outer aperture system so that they collect the light scattered on the sample within set, different angle ranges, wherein the first inner aperture system and the second outer aperture system are formed and arranged circularly and concentrically around the axis of the measuring cell. Use of the apparatus and a method that makes use of the apparatus are also disclosed.

13 Claims, 5 Drawing Sheets

40: outer aperture system
41: inner aperture system
42: upper part of the portion of the support for fixing the measuring cell
43a: capillary tube for discharging the liquid medium with the sample
43b: capillary tube for feeding the liquid medium with the sample
44a: flat seal
44b: flat seal
45: detector
46: laser
47: laser beam
48: lower part of the portion of the support for fixing the measuring cell
49: measuring cell
49a: bore hole
50: support

Figure 5

50: support
51: laser
52: laser beam
53: support for fixing the measuring cell
54: inner aperture system
55: outer aperture system
56: detector
57: scattered light beam
58: radial grooves
59: inlet openings for the laser beam
60: outlet openings for the laser beam

APERTURE SYSTEM FOR MULTI-ANGLE LIGHT SCATTERING DETECTORS

CROSS-REFERENCE TO RELATED APPLICATIONS

This application claims the benefit of priority to European patent application serial number EP11185620, which was filed on Oct. 18, 2011.

TECHNICAL FIELD

The invention relates to an apparatus for measuring the light scattering properties of a sample in a liquid medium, the use of this apparatus and a method for measuring the light scattered on a sample located within a liquid medium.

PRIOR ART

Measurement of static light scattering is used in order to characterize (size, mass, shape and structure) molecules or colloidal substances. This is an absolute quantification which goes without any previous calibration or use of standard samples. A sample is illuminated with a laser beam, and the scattered light is measured at different scattering angles.

The principle of light scattering is widespread in nature. It can thus be observed e.g. as the sun sets or when dust particles become visible. Light beams strike a strongly scattering medium and are deflected from their geometrically prescribed path by particles. The intensity of the light beams is thereby reduced by absorption and scattering. Scattering is the basis for different physical phenomena, such as e.g. deflection, diffraction and reflection.

Scattering can be subdivided into inelastic, quasi-elastic and elastic scattering which are differentiated by their frequency shift. With inelastic scattering a frequency shift of approximately $10^{11}$ to $10^{13}$ Hz occurs. With quasi-elastic scattering, with which light additionally interacts with translation and rotation quanta of a molecule, a frequency shift of 10 to $10^6$ Hz occurs. With elastic light scattering (e.g. static light scattering) there is no change to the wavelength (also called coherent scattered radiation).

The underlying principle of light scattering can be illustrated by a very small, optically isotropic gas molecule. The electrons of the molecule are caused to vibrate with the frequency of the exciting light source by the electromagnetic wave that occurs. In turn, the oscillating dipole thus produced radiates electromagnetic radiation of the same frequency, the intensity of the radiation depending on the strength of the induced dipole, i.e. the more polarizable the molecule is, the stronger the dipole and the greater the intensity of the emitted radiation.

If a sample, for example a suspension, in which there are a number of macromolecules, is illuminated by a laser beam, every macromolecule emits radiation. The sum of the intensities of the emitted radiation is in proportion to the concentration of the macromolecules in the suspension and the molar mass of the molecules.

Furthermore, the size of the molecules contained in the colloid can be calculated from the angle dependence of the scattered light intensities because the light scattered on the different scatter centers in the macromolecule interferes and produces an angle-dependent scatter pattern. The average values of the size of the particles located in a measuring cell are thereby respectively determined.

Measuring instruments are described in the prior art which measure the scattering properties of colloidal liquids and use this to characterize the properties of the material. Thus, for example, EP 0 182 618 discloses an apparatus which describes the measurement of the static light scattering by means of a measuring cell. The measuring cell can be coupled to a chromatographic structure so that the particles, separated according to size, flow through the measuring cell. For this purpose a round glass cell is provided with a longitudinal bore hole through which a flow of liquid containing the particles is conveyed and is illuminated with a laser beam. Detectors, which record the scattered light, are arranged at different angles around the round glass cell.

This technology was described for the first time in U.S. Pat. No. 4,616,927 and EP 0 182 618. The measurement of the scattered light at a number of different angles is disclosed here. The observed scattering region is restricted to a few nanoliters by apertures.

In EP 0 626 064 a further development is described in which measurements are taken at 2 angles, the light scattered at 15 degrees being collected by means of a lens and aperture system.

In U.S. Pat. No. 6,052,184 the scattered light is collected by means of fiber optics, the latter only observing a very small area of liquid however. The flow of liquid is conveyed here perpendicularly to the incident light beam.

A further apparatus, in which the flow of liquid is also conveyed through the measuring cell perpendicularly to the incident light beam, is described in WO 2010/036736. The necessary fixation of the measuring cell in an accurately fitting way is implemented by means of appropriate projections of the support device which extend into the bore hole of the measuring cell.

In the apparatuses described in WO 2010/036736 cylindrical, cuvette-like glass measuring cells with a curved outside are used which are illuminated horizontally with a laser beam but are flowed through vertically.

In order to guarantee the formation of a liquid flow with a laminar flow profile within this type of measuring cell, the liquid flow can be divided with the aid of an appropriate guide into three individual liquid flows which are each conveyed through one of three radially arranged grooves into the measuring cell. This form of flow into the measuring cell is disclosed, for example, in WO 98/52013.

However, when using the glass measuring cells described in WO 2010/036736 for the measurement of static multi-angle light scattering within an angle range of less than 7° to above 164° the following problems occur.

The diameter of the inner bore hole, and so the volume of the cuvette-like measuring cells should basically be kept as small as possible in order to avoid peak widenings in the measuring signal obtained and in order to maintain a homogeneous flow within the measuring cell. This leads, however, to the relocation of remissions (non-directed reflections), which are caused by the laser beam on the boundary surfaces between the glass of the measuring cell and the liquid flowing through and containing the sample, close to the scattering center/scattering centers of the respective sample within the measuring cell. For this reason, when using measuring cells with a small volume, interference of the scattering light signal to be recorded by the remissions described occurs. Due to minimal laser position fluctuations, the remissions are not stable and lead to vibrations, instabilities and overdrives in the detector signals when they reach the detectors.

Basically, in order to measure the angle-dependent scattered light intensity of a sample two points are particularly critical:

1. Only the scattered light from the smallest possible angle range may fall into each detector.

2. Light that could fall into the respective detector due to remissions on the measuring cell glass/liquid (containing the sample) or measuring cell glass/air boundary surfaces must be shielded.

Previously, the blocking required for this purpose was achieved with the aid of bore holes within a device surrounding the measuring cell. The problem here is that light within these bore holes is reflected on the respective wall and so, even if in reduced form, can fall into individual detectors and distort the measurements. Since the bore holes on the one hand must have a small diameter, but on the other hand must be relatively long in order to be able to restrict the angle range of the incident scattered light sufficiently, it is not possible to coat the inside of the bore holes homogeneously with a light-absorbing substance.

DESCRIPTION OF THE INVENTION

It is the object of the invention to provide a measuring apparatus for measuring static multi-angle light scattering in an angle range of less than 7° to above 164° in which a translucent measuring cell is used which is filled with a sample or through which a sample flows, and which is illuminated with a laser beam transversely to the filling direction or transversely to the flow direction of the sample, and which does not have the disadvantages described for the apparatuses known from the prior art with regard to the disrupting influence of scattered light from non-observed angle ranges and remissions, and which achieves improvement of the measuring sensitivity.

This object is achieved by the apparatus according to claim 1 and the method according to claim 8.

According to the invention, an apparatus for measuring the light scattering properties of a sample in a liquid medium, wherein the liquid medium with the sample is illuminated by a laser beam in a measuring cell transversely to the direction of filling the liquid medium in the measuring cell or transversely to the flow direction of the liquid medium within the measuring cell, comprising a laser, a cylindrical measuring cell, a first inner aperture system, a second outer aperture system and at least two detectors, wherein the detectors are arranged outside of the second outer aperture system so that they collect the light scattered on the sample within set, different angle ranges, is characterized in that the first inner aperture system and the second outer aperture system are formed and arranged circularly and concentrically around the axis of the measuring cell.

Within the framework of the present invention, it was surprisingly found that when detecting light scattered on a sample (scattered light) at a specific angle, a system comprising two apertures arranged one behind the other is suitable for minimizing disruptive influences due to scattered light from angle ranges not observed and remissions. Scattered light from non-observed angle ranges and remissions, i.e. light deflected at the boundary surfaces between the measuring cell and the liquid medium flowing through and containing the sample, can propagate in the dual-aperture system of the apparatus according to the invention between the apertures, but no longer reach the detectors.

In particular, by means of a first inner aperture system that is arranged concentrically around the axis of the measuring cell, a restriction to a defined scattering volume is first of all carried out, and at the same time a specific angle range to be detected is also selected. A second outer aperture system that is arranged close to the detectors concentrically around the first inner aperture system then guarantees that only light of a specific angle range which has passed the first inner aperture system falls into the corresponding detector, and that the light deflected on the boundary surfaces between the measuring cell and the liquid medium flowing through and containing the sample thereby causing remissions is blocked out.

Correspondingly, the apparatus according to the invention contains a dual-aperture system comprising a first inner and a second outer aperture system which are both formed and arranged circularly and concentrically around the axis of the measuring cell.

In connection with the present invention, the term "circular" in relation to the first inner and the second outer aperture system means that each of them describes the form of the lateral area of a right circular cylinder.

The two aperture systems each have a number of aperture openings arranged one next to the other and are preferably integrally formed, wherein the number of aperture openings in each of the two aperture systems corresponds to the number of detectors used in the apparatus according to the invention. The aperture systems can be produced from both plastic such as e.g. PEEK, PMMO, PA, etc., and metal such as e.g. aluminum, different steels such as e.g. Invar, stainless steel, titanium and non-ferrous metals such as e.g. brass.

The first inner aperture system is arranged close to the measuring cell, concentrically around its axis, and is in the region of 0.1-1 mm, preferably 0.4-0.8 mm and particularly preferably 0.4-0.6 mm away from the measuring cell. The second outer aperture system is arranged close to the detectors, concentrically around the first inner aperture system, and is in the region of 1-60 mm, preferably 15-45 mm, and particularly preferably 32-36 mm away from the detectors. The distance between the first inner and the second outer aperture system is 15-20 mm, preferably 16-17 mm and particularly preferably 16.4-16.6 mm.

In one preferred embodiment, the distance between the first inner aperture system and the measuring cell is 0.4-0.6 mm, preferably 0.5 mm, the distance between the second outer aperture system and the detectors is 32-36 mm, preferably 34.2 mm, and the distance between the first inner and the second outer aperture system is 16.4-16.6 mm, preferably 16.5 mm.

In one embodiment, the first inner and the second outer aperture system are both formed as slot apertures, wherein the number of slots in the two aperture systems corresponds to the number of detectors used which are arranged around the second outer aperture system. In addition, each of the aperture systems has an inlet opening and an outlet opening for the laser beam. The individual slots are arranged transversely, i.e. at an angle of 90°, to the circular plane of the circularly formed aperture systems and thus form a comb-shaped aperture.

In an alternative embodiment, the aperture openings in the first inner and the second outer aperture system can each be in the form of pinhole apertures, wherein the individual aperture holes can be rectangular, square or round.

Preferably, the first inner and the second outer aperture system are both in the form of comb-shaped slot apertures.

According to the invention, the measuring cell, the first inner and the second outer aperture system as well as the detectors lie on an optical axis so that the individual detectors collect set, different angle ranges of the light, which is scattered on the sample and leaves the measuring cell. This arrangement makes it possible that only light of a specific angle range falls into the corresponding detector and that scattered light from angle ranges being not observed and remissions are blocked out.

In particular, the measuring cell, the first inner and the second outer aperture system as well as the detectors are arranged in a plane (in the following also referred to as the detection plane) such that the measuring cell, the respective slots in the two aperture systems and the detectors lie on a line, preferably a straight line, and that the individual detectors collect set, different angle ranges of the light, which is scattered on the sample and leaves the measuring cell.

In one preferred embodiment, the slots of the two aperture systems are arranged one behind the other and not offset, and the straight line extends vertically from the curved outside of the measuring cell.

The detectors are arranged at different, set angles of 3° to 172°, preferably of 7° to 164° in relation to the optical path of the laser through the measuring cell, outside of the second outer aperture system around the whole measuring cell in the detection plane so that they collect light scattered on the sample at the respective angles and in restricted angle ranges around this angle. Preferably the detectors are arranged circularly and concentrically around the measuring cell in the detection plane.

The apparatus according to the invention thus makes it possible to observe the light scattered on the sample within set, different angle ranges of 3° to 172° and preferably of 7° to 164°.

In connection with the present invention, the term "angle range" indicates a specific angle in relation to the optical path of the laser through the measuring cell within the detection plane including a range around this angle of +/−0.95° and preferably of +/−0.15°.

The apparatus according to the invention comprises 2-25 and preferably 7-21 detectors.

In one preferred embodiment, the apparatus according to the invention comprises 7, 14 or 21 detectors and particularly preferably 21 detectors.

In order to enable the installation of up to 25 detectors in the detection plane of the apparatus according to the invention, the detectors are arranged alternately around the whole measuring cell, wherein "alternately" means that detectors with adjacent observation angles are always arranged on opposite sides of the measuring cell within the detection plane.

A detector is an apparatus described in the prior art which converts incident light into electric signals depending on its intensity, and this can be implemented e.g. by means of light-sensitive diodes or photomultipliers and conveys it to corresponding processing devices which convert the measured signals into the desired units. Particularly preferred detectors are hybrid photodiodes. These are a combination of a photodiode with an integrated amplifier. This type of combination makes possible great sensitivity with a small amount of dark noise and a good price/performance ratio.

In one embodiment, independently of the observed angle range of the light scattered on the sample, the slots of the first inner and the second outer aperture system all have the same width in a range of 0.1-3.0 mm, preferably 0.2-1.5 mm, and particularly preferably 0.2-0.8 mm.

In one preferred embodiment, depending on the observed angle range of the light scattered on the sample, the first inner and the second outer aperture system have different slot widths, wherein the slot widths of the first inner and the second outer aperture system is the same for a given observed angle range of the light scattered on a sample. By means of the different slot widths it is guaranteed that the differences in the intensity of the scattered light falling into the detectors is as low as possible for the respectively observed angle ranges.

Basically, a sample scatters irradiated light in all directions, the scattered light intensity for the respectively observed angle ranges depending on the size of the sample molecules or particles. Therefore, among other things a different scattered light intensity can result from the fact that irradiated light is not scattered equally on a sample in all directions, depending on the size of individual sample molecules or particles, but directed scattering occurs which leads to a greater scattered light intensity with smaller observation angles. With the same size of sample molecules or particles, depending on the observation angle a different scattering volume is moreover produced which, depending on the angle, also leads to different scattered light intensities. Here the scatter volume and so the scattered light intensity is basically greater for smaller observation angles than for larger observation angles. By using different slot widths, depending on the observed angle range of the light scattered on a sample, the different scattered light intensities can be leveled out within certain limits so that the differences in intensity of the scattered light falling into the detectors are as small as possible for the respectively observed angle ranges.

In the case of small and very large observation angles, the light of the laser beam passing out of the measuring cell and used to illuminate the sample additionally contributes to increasing the scattered light intensity.

Basically, in the case of higher scattered light intensities as can occur e.g. for smaller angle ranges, slots with a smaller width are used in the dual aperture system of the apparatus according to the invention.

In one particularly preferred embodiment, the following observation angles and slot widths are used:

TABLE 1

Observation angles and slot widths

| Observation angle | Slot width [mm] |
|---|---|
| 3°-7° | 0.2 |
| 12° | 0.3 |
| 20° | 0.5 |
| 28°-148° | 0.8 |
| 156° | 0.7 |
| 164°-172° | 0.5 |

The apparatus according to the invention is a multi-angle light scattering detector (MALS [Multi-Angle Light Scattering] detector) which is equipped with the previously described dual-aperture system.

All molecules and particulate particles with a size of 10 nm-1000 nm, preferably 26.6 nm-532 nm, and/or a molecular weight of 1000 Da-$10^9$ Da are suitable as a sample of which the light scattering properties can be measured with the apparatus according to the invention. Samples for measuring with the apparatus according to the invention are e.g. proteins from the areas of the pharmaceutical industry and research, nanoparticles and carbon nanotubes as well as natural and synthetic polymers.

The sample can be dissolved or suspended in the liquid medium.

Aqueous and non-aqueous organic solvents can be used as a liquid medium for use in the apparatus according to the invention. Preferably, solvents which are generally used in High Performance Liquid Chromatography (HPLC) or Field-Flow Fractionation (FFF) are used. Examples include aqueous solutions of 0.5-5 g/l NaCl and 0.1-5 g/l sodium dodecyl sulfate (SDS) and the organic solvents tetrahydrofuran (THF), toluene, acetone, methanol, ethanol, chloroform, dimethyl formamide (DMF) and dimethyl sulfoxide (DMSO) and mixtures of the latter.

In the apparatus according to the invention, a cylindrical measuring cell is used. In connection with the present invention the term "cylindrical measuring cell" means a measuring cell which has the shape of a right circular cylinder.

A measuring cell for use in the apparatus according to the invention has a central bore hole along the axis of the measuring cell. The bore hole allows the liquid medium that contains the sample to be fed in and discharged.

The bore hole of the measuring cell of the apparatus according to the invention is either an indentation or a perforation with a round cross-section which is arranged concentrically to the axis of the measuring cell so that the measuring cell has either one or two round openings.

In one preferred embodiment, the bore hole is a perforation.

Furthermore, a measuring cell for use in the apparatus according to the invention is formed from a translucent material that allows the laser beam to pass in, through and out.

In one embodiment, the measuring cell is produced from glass, polymer or a combination of said materials or a liquid and has a refractive index that substantially corresponds to the refractive index of the liquid medium that contains the sample to be measured and which is higher than the refractive index of air. In one preferred embodiment the measuring cell is made from glass.

In connection with the present invention, the term "substantially corresponds" in relation to the refractive index of the measuring cell and the refractive index of the liquid medium means that the respective refractive indices are as similar as possible and differ from one another by no more than at most 0-0.5, preferably at most 0-0.3 and even more preferably at most 0-0.2. In one particularly preferred embodiment the difference is no more than at most 0-0.13.

The refractive index, previously the refraction coefficient, is a material constant and describes the propagation of light, i.e. electromagnetic waves, in an optically dense medium. It can be determined from the ratio between the phase velocity of the light in vacuum and its phase velocity in the respective medium. Thus, the refractive index e.g. for visible light in vacuum is precisely 1, for air at sea level 1.000292, for quartz glass 1.46 and for polymers approximately 1.5.

The term "polymer" designates a chemical compound that consists of chains or branched molecules which are constructed from the same or similar units. Examples of these are polymers made of polyethylene, polypropylene, polyvinyl chloride, polymethylmethacrylate, polyester or polyurethane.

In one embodiment, in the region of its curved surface the measuring cell through which the light scattered on the sample leaves is optically polished in order to minimize angle falsifications or the scattering of the light on the optical transitions. The surface can be polished by known standard methods. The surface e.g. of quartz glass can thus be processed by flame polishing and mechanical polishing. Polishing by means of laser beams is also possible.

In order to guarantee interference-free sample measuring, it is preferred according to the invention to avoid turbulent flows within the bore hole of the measuring cell during the sample measurement and instead to produce a laminar flow profile within the bore hole.

In one embodiment, the apparatus according to the invention therefore further comprises, in addition to a laser a cylindrical measuring cell, a first inner aperture system, a second outer aperture system and the at least two detectors, a support for holding the laser, the cylindrical measuring cell, the first inner aperture system, the second outer aperture system and the at least two detectors, the support being characterized in that in the region for holding the measuring cell has three radially arranged grooves via which the liquid medium that contains the sample to be measured is conveyed into the bore hole of the measuring cell. In detail, the three radially arranged grooves run in a star shape within a surface of the support arranged plane-parallel to one of the two flat sides of the cylindrical measuring cell and meet in the region of the bore hole of the measuring cell. Such an arrangement is described, for example, in WO 98/52013.

The liquid medium that contains the sample is split with the aid of a suitable guide into three liquid flows which are each conveyed through one of the three grooves along one of the two flat sides of the cylindrical measuring cell in the direction of the central bore hole of the measuring cell. In the region of the central bore hole of the measuring cell the three liquid flows are unified and conveyed, preferably from the bottom to the top, into the bore hole of the measuring cell. This form of flow into the central bore hole of the measuring cell of the apparatus according to the invention guarantees the formation of a liquid flow with a laminar flow profile in the bore hole of the measuring cell during the sample measurement.

In one preferred embodiment, the three radially running grooves are each arranged at an angle of 120° in relation to one another.

In WO 2010/036736, an apparatus is described in which the necessary fixation of the employed measuring cell in the support is implemented by means of suitable projections of the support device which extend into the bore hole of the measuring cell. In contrast to this, the measuring cell in the apparatus according to the invention is fixed in the desired position within the support from the outside by a corresponding shape of the support. In particular, the support is formed such that it is suitable for holding the measuring cell in an accurately fitting way and encloses at least part of the round outside, i.e. the lateral area, of the cylindrical measuring cell, wherein the specific shape of the support has no negative impact upon the laser beam as it passes in, through and out of the measuring cell. With the aid of two circular flat seals arranged on the flat sides of the cylindrical measuring cell said measuring cell is sealed. The flat seals have the same diameter as the measuring cell and have a corresponding central, round opening in the region of the bore hole of the measuring cell. In comparison with the apparatus known from WO 2010/036736, the support of the apparatus according to the invention is therefore characterized by a more simple construction that can additionally be produced more easily and less expensively.

In a further preferred embodiment, the apparatus according to the invention, comprising a support for holding the laser, the cylindrical measuring cell, the first inner aperture system, the second outer aperture system and the at least two detectors, is therefore characterized in that in the region for holding the measuring cell the support has three radially arranged grooves via which the liquid medium that contains the sample to be measured is conveyed into the measuring cell, and that the measuring cell is fixed in the desired position within the support with the aid of a molding in the support, wherein the lateral area of the measuring cell is partially enclosed by the support, and the measuring cell is sealed by means of two flat seals arranged on the flat sides of the cylindrical measuring cell.

In the apparatus according to the invention, the light scattered on the sample (scattered light) is produced by means of a laser beam with which the sample located within the measuring cell is illuminated, wherein the coherence length of the laser beam preferably is greater than the maximum size of the sample to be measured. Different lasers such as e.g. diode lasers, solid state lasers or gas lasers can be used as the laser beam source. Preferably, lasers with a wavelength of 245 nm to 1200 nm, preferably 375 nm to 1064 nm and more preferably 320 nm to 680 nm are used. Particularly preferably, lasers with a wavelength of 532 nm are used.

The sample located within the measuring cell is illuminated transversely to the direction of filling the liquid medium with the sample in the measuring cell or transversely to the flow direction of the liquid medium with the sample within the measuring cell. In detail, the liquid medium with the sample that is conveyed along the axis of the measuring cell into/through the bore hole of the measuring cell is illuminated by a laser beam in the bore hole of the measuring cell transversely to the axis of the measuring cell.

In connection with the present invention the terms "transversely to the direction of filling" and "transversely to the flow direction" in relation to the illumination direction mean that the plane in which the vector of the filling direction or the flow direction lies and the plane in which the vector of the laser beam with which the sample is illuminated lies stand perpendicularly or substantially perpendicularly one over the other, i.e. they are arranged at an angle of 90°+/−2° in relation to one another.

In a further embodiment, the present invention relates to a method for measuring the light scattered on a sample located within a liquid medium. Here the method makes use of the previously described apparatus according to the invention with its individual components, and the terms explained above and the definitions specified above also relate to the method according to the invention.

The method according to the invention comprises the following steps:

a) introducing the liquid medium that contains the sample into a cylindrical measuring cell, b) illuminating the sample located within the measuring cell transversely to the direction of filling the liquid medium in the measuring cell or transversely to the flow direction of the liquid medium within the measuring cell with a laser beam, and c) detecting the resulting scattered light beams with at least two detectors arranged circularly and concentrically around the measuring cell and which collect the light scattered on the sample within set, different angle ranges, and is characterized in that the detectors are shielded from scattered light beams, which do not come within the respectively set angle ranges, and remissions by a first inner aperture system and a second outer aperture system which are formed and arranged circularly and concentrically around the axis of the measuring cell.

In one preferred embodiment, the method according to the invention is characterized in that the cylindrical measuring cell into which the liquid medium that contains the sample is introduced has a bore hole along its axis and is formed from a translucent material, the liquid medium that contains the sample is introduced into the bore hole along the axis of the measuring cell and the sample located within the bore hole of the measuring cell is illuminated transversely to the axis of the measuring cell by a laser beam.

The method according to the invention makes it possible to measure the scattered light which is produced by illuminating a sample within a liquid medium with a laser beam. For this purpose a liquid medium that contains the sample is conveyed through a central bore hole that runs along the axis through a cylindrical measuring cell. The laser beam runs transversely to this bore hole and illuminates the liquid medium with the sample, by means of which light is scattered on the individual sample molecules or particles. Light-sensitive detectors that receive the scattered light are arranged around the measuring cell. The detectors are located in a plane with the measuring cell. The light received by the detectors is preferably converted into electric signals and is passed on to corresponding processing devices for calculation of the desired properties of the sample molecules or particles such as e.g. size, mass, shape and structure. There is also located in a plane and on an optical axis with the measuring cell and the detectors, between the measuring cell and the detectors, the previously described dual-aperture system comprising a first inner aperture system and a second outer aperture system which are both formed and arranged circularly and concentrically around the axis of the measuring cell. The dual-aperture system minimizes distracting influences of scattered light from non-observed angle ranges and remissions and thus enables the interference-free measurement of scattered light of specific, set angle ranges.

In a further embodiment, the present invention relates to the use of the apparatus according to the invention for measuring the light scattered on a sample located within a liquid medium.

By means of the light scattering properties of a sample e.g. its size, mass, shape and structure can then be determined. In order to enable significant measurement of the light scattering properties, the individual sample molecules and particles must be present during the measurement in fractions each having a substantially uniform particle size and/or a substantially uniform molar mass.

In connection with the present invention, the terms "substantially uniform particle size" and "substantially uniform molar mass" designate a monomodal particle size distribution or a monomodal molar mass distribution, wherein the particle size and the molar mass of individual sample molecules and particles differ by at most +/−15%, preferably by at most +/−10%, from the respective average value.

The fractionation of corresponding sample mixtures for obtaining samples each having a substantially uniform particle size and/or a substantially uniform molar mass can be implemented by means of chromatographic, quasi-chromatographic or other suitable separating methods.

The methods of High Performance Liquid Chromatography (HPLC) can for example be used as chromatographic separating method. In one preferred embodiment Size Exclusion Chromatography (SEC) or Gel Permeation Chromatography (GPC) are used as specific examples of possible HPLC methods in the present invention.

One suitable quasi-chromatographic separating method is Field-Flow Fractionation (FFF). In one preferred embodiment symmetrical flow field-flow fractionation, asymmetrical flow field-flow fractionation, sedimentation field-flow fractionation, such as e.g. centrifugal field-flow fractionation, and thermal field-flow fractionation are used for the fractionation of a sample in the present invention. Symmetrical or asymmetrical flow field-flow fractionation is particularly preferably used.

In one embodiment the measurement of the light scattered on the sample is taken by means of a batch measurement. For this purpose, the liquid medium that contains the sample is filled in the bore hole of the measuring cell following previous fractionation in a previously set amount. Next, the sample is measured, wherein no flow of the liquid medium with the sample through the measuring cell takes place during the measurement, so that the liquid medium with the sample is unmoved within the measuring cell during the measurement.

In a further embodiment, the measurement of the light scattered on the sample is taken by means of online measurement. For this purpose, the liquid medium with the sample is conveyed continuously through the bore hole of the measuring cell following previous fractionation, and the measurement is taken over the entire test period. The sample flow through the measuring cell can be produced e.g. by means of HPLC or FFF equipment. Preferably, the sample flow through the measuring cell is produced by means of the HPLC or FFF equipment which has been used for the previously described preceding fractionation of the sample.

In one preferred embodiment, the measurement of the light scattered on the sample is taken by means of online measurement.

In a further embodiment, the apparatus according to the invention can for this purpose be coupled to HPLC equipment such as e.g. SEC or GPC equipment or FFF equipment. Preferably, the apparatus according to the invention is coupled to FFF equipment, particularly preferably to FFF equipment for symmetrical flow field-flow fractionation, asymmetrical flow field-flow fractionation, sedimentation field-flow fractionation such as e.g. centrifugal field-flow fractionation and thermal field-flow fractionation, and particularly preferably to FFF equipment for symmetrical or asymmetrical flow field-flow fractionation.

In an alternative embodiment, batch measurements can also be taken on an unfractionated sample.

WAYS OF IMPLEMENTING THE INVENTION

Figure 1:
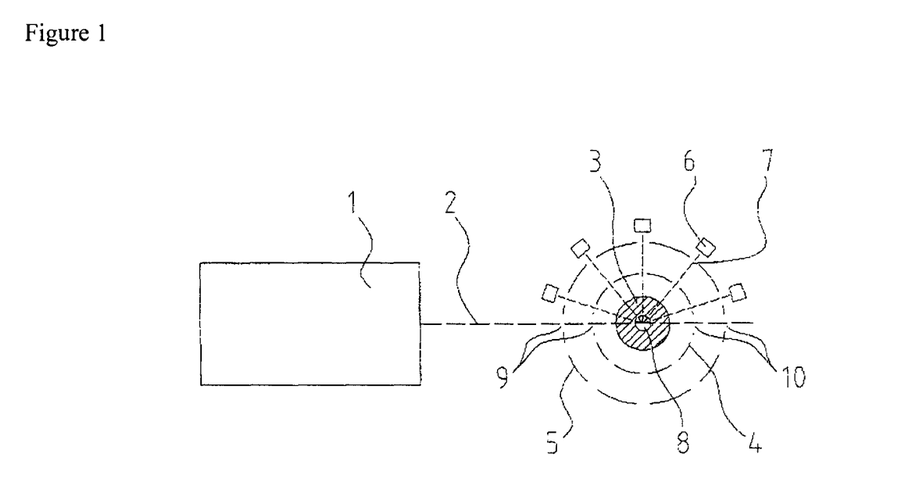
FIG. 1 shows the top view of a preferred embodiment of the apparatus according to the invention.

FIG. 1 shows a top view of the schematic structure of a preferred embodiment of the apparatus according to the invention.

The apparatus according to the invention shown comprises a laser (1), a cylindrical measuring cell (3) with a central bore hole (8) along its axis, a first inner aperture system (4) and a second outer aperture system (5) which are both formed and arranged circularly and concentrically around the axis of the measuring cell (3), and five detectors (6), the detectors (6) being arranged circularly and concentrically around the axis of the measuring cell (3) outside of the second outer aperture system (5) so that they collect the light scattered on the sample in set, different angle ranges.

The first inner aperture system (4) and the second outer aperture system are in the form of comb-shaped slot apertures and both additionally have an inlet opening (9) and an outlet opening (10) for the laser beam (2).

The laser beam (2) runs transversely to the central bore hole (8) of the measuring cell (3) and illuminates a liquid medium that contains a sample and is located within the central bore hole (8) of the measuring cell (3). In this way, light is scattered on the individual sample molecules or particles. The scattered light beams (7) produced are received by light-sensitive detectors (6) arranged circularly and concentrically around the measuring cell, wherein the detectors (6) are shielded from scattered light beams, which do not come within the respectively set angle ranges, and remissions by the first inner aperture system (4) and the second outer aperture system (5).

Figure 2:
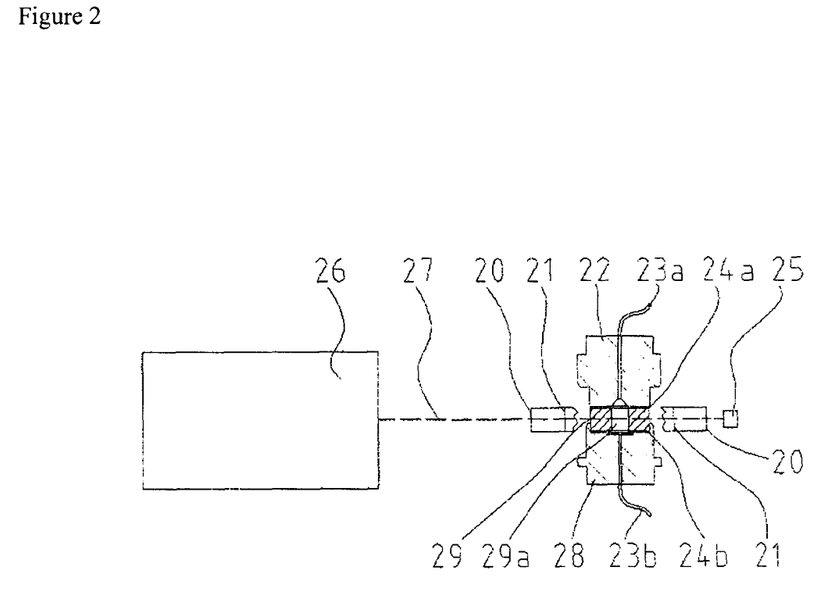
FIG. 2 shows the side view of a preferred embodiment of the apparatus according to the invention.

FIG. 2 shows a side view of the schematic structure of a preferred embodiment of the apparatus according to the invention.

The apparatus according to the invention shown comprises a laser (26), a cylindrical measuring cell (29) with a central bore hole (29a) along its axis, a first inner aperture system (21) and a second outer aperture system (20) which are both formed and arranged circularly and concentrically around the axis of the measuring cell (29), and a number of detectors (25) (for illustratory reasons, only one detector is shown here), wherein the detectors (25) are arranged outside of the second outer aperture system (20) so that they collect the light scattered on the sample within set, different angle ranges.

The support of the apparatus according to the invention is formed such that it comprises an upper part (22) and a lower part (28) for holding the measuring cell (29) in an accurately fitting way and thus for fixing of the measuring cell (29) in the support. The lower part (28) has a molding in which the measuring cell is held in an accurately fitting way and which encloses at least part of the round outside, i.e. the lateral area, of the cylindrical measuring cell (29). The height of the molding is chosen such that there is no negative impact upon the laser beam (27) passing in, through and out of the measuring cell (29). The upper part (22) has a flat lower side and does not enclose the measuring cell. The measuring cell (29) is securely fixed between the lower part (28) and the upper part (22) and is sealed with the aid of two circular flat seals (24a, 24b) arranged on the flat sides of the cylindrical measuring cell (29). The flat seals (24a, 24b) have the same diameter as the measuring cell (29) and have a corresponding central, round opening in the region of the bore hole (29a) of the measuring cell.

In the embodiment of the apparatus according to the invention shown a liquid medium that contains the sample is conveyed during the measurement through the bore hole (29a) of the measuring cell (29) by means of a feed capillary tube (23b) and a discharge capillary tube (23a).

Figure 3:
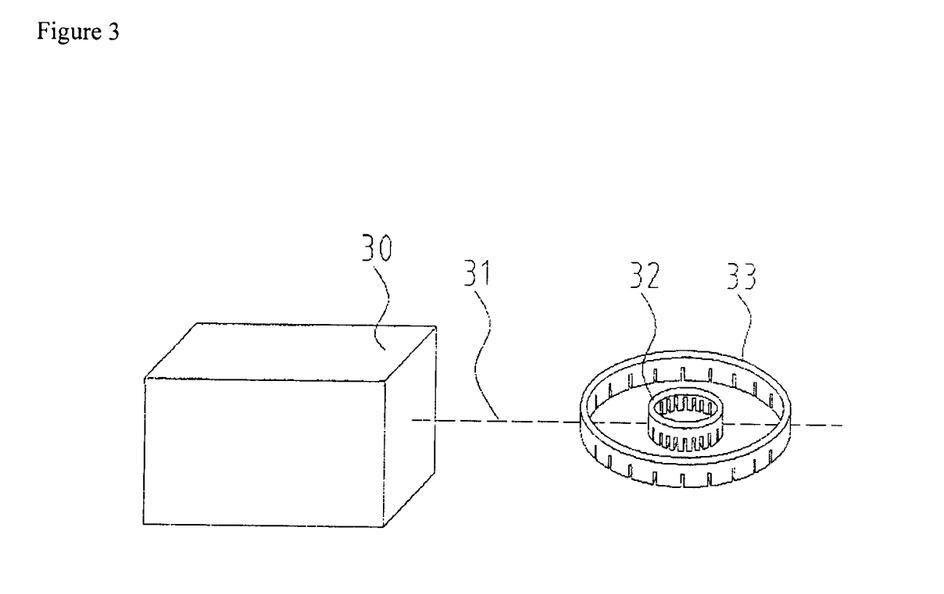
FIG. 3 shows the three-dimensional view of the dual-aperture system of the apparatus according to the invention.
Figure 4:
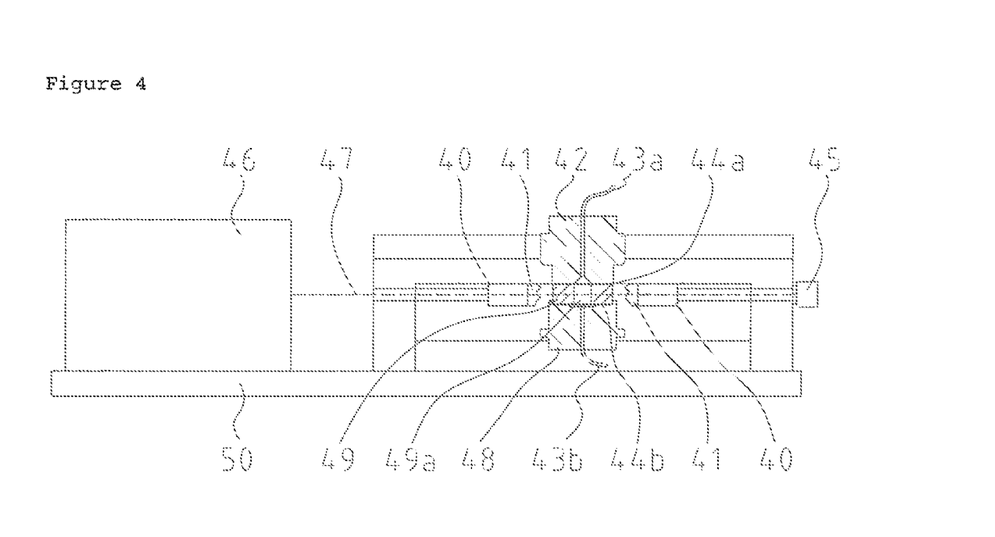
FIG. 4 shows a side view of an embodiment of the apparatus according to the invention.
Figure 5:
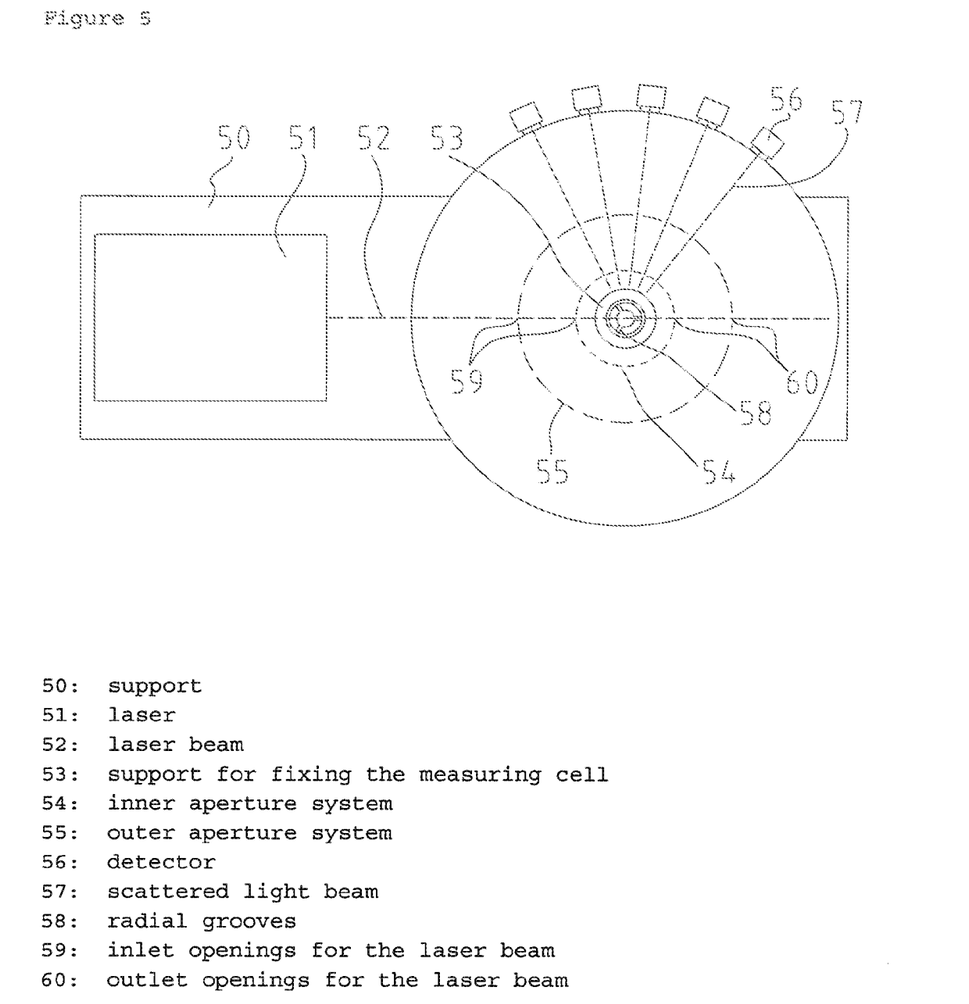
FIG. 5 shows a top view of an embodiment of the apparatus according to the invention.

FIG. 3 shows the three-dimensional view of a first inner aperture system (32) and a second outer aperture system (33) which are formed and arranged circularly and concentrically and together form a dual-aperture system of the apparatus according to the invention. The two aperture systems (32, 33) shown each are in the form of comb-shaped slot apertures.

PARTS LIST

1: laser
2: laser beam
3: measuring cell
4: inner aperture system
5: outer aperture system
6: detector
7: scattered light beam
8: bore hole
9: inlet openings for the laser beam
10: outlet openings for the laser beam
20: outer aperture system
21: inner aperture system
22: upper part of the portion of the support for fixing the measuring cell
23a: capillary tube for discharging the liquid medium with the sample
23b: capillary tube for feeding the liquid medium with the sample 24a: flat seal
24b: flat seal
25: detector
26: laser
27: laser beam
28: lower part of the portion of the support for fixing the measuring cell
29: measuring cell
29a: bore hole
30: laser
31: laser beam
32: inner aperture system
33: outer aperture system

The invention claimed is:

1. Apparatus for measuring light scattering properties of a sample in a liquid medium, wherein the liquid medium with the sample is illuminated by a laser beam (2) in a measuring cell (3) transversely to a direction of filling the liquid medium in the measuring cell or transversely to a flow direction of the liquid medium within the measuring cell (3), comprising a laser (1), a cylindrical measuring cell (3), a first inner aperture system (4), a second outer aperture system (5) and at least two detectors (6), wherein
the detectors (6) are arranged outside of the second outer aperture system (5) so that the detectors (6) collect the light scattered on the sample within set, different angle ranges,
characterized in that the first inner aperture system (4) and the second outer aperture system (5) are formed and arranged circularly and concentrically around a longitudinal axis of the measuring cell (3); and
further characterized in that the first inner aperture system (4) and the second outer aperture system (5) are both formed as slot apertures, wherein the number of slots in the two aperture systems corresponds to the number of detectors (6), and each of the aperture systems additionally has an inlet opening (9) and an outlet opening (10) for the laser beam (2); and
further characterized in that the first inner aperture system (4) and the second outer aperture system (5) have different slot widths depending on the observed angle range of the light scattered on the sample, wherein the slot widths of the first inner aperture system (4) and of the second outer aperture system (5) are the same for a given observed angle range of the light scattered on the sample.

2. The apparatus according to claim 1, wherein
the cylindrical measuring cell (3) has a bore hole (8) along its axis which allows feeding and discharging of the liquid medium that contains the sample and is formed from a translucent material that allows the laser beam (2) to pass in, through and out, and wherein
the liquid medium with the sample is conveyed along the axis of the measuring cell into/through the bore hole (8) of the measuring cell (3) and is illuminated in the bore hole (8) of the measuring cell (3) transversely to the axis of the measuring cell (3) by the laser beam (2).

3. The apparatus according to claim 1, characterized in that the measuring cell (3), the first inner aperture system (4) and the second outer aperture system (5) as well as the detectors (6) lie on an optical axis so that the individual detectors (6) collect set, different angle ranges of the light, which is scattered on the sample and leaves the measuring cell (3).

4. The apparatus according to claim 1, characterized in that the measuring cell (3) is produced from glass, polymer or a combination of said materials or a liquid and has a refractive index that substantially corresponds to the refractive index of the liquid medium that contains the sample to be measured and which is higher than the refractive index of air.

5. The apparatus according to claim 1, characterized in that the apparatus enables observation of the light scattered on the sample within set, different angle ranges of 7° to 164°.

6. The apparatus according to claim 1, characterized in that the apparatus comprises 2-25 detectors (6).

7. The apparatus according to claim 1, further comprising a support for holding the laser (1), the cylindrical measuring cell (3), the first inner aperture system (4), the second outer aperture system (5) and the at least two detectors (6), characterized in that
in a region for holding the measuring cell (3) the support has three radially arranged grooves via which the liquid medium that contains the sample to be measured is conveyed into the measuring cell (3), and
the measuring cell is fixed in a desired position within the support with the aid of a molding in the support, wherein a lateral area of the measuring cell is partially enclosed by the support, and the measuring cell is sealed by means of two flat seals arranged on flat sides of the cylindrical measuring cell.

8. A method for measuring light scattered on a sample located within a liquid medium, comprising the following steps:
a) introducing the liquid medium that contains the sample into a cylindrical measuring cell (3),
b) illuminating the sample to produce scattered light, the sample being located within the measuring cell (3) transversely to the direction of filling the liquid medium in the measuring cell or transversely to the flow direction of the liquid medium within the measuring cell (3) with a laser beam (2),
c) passing scattered light through a first inner aperture system (4) and then a second outer aperture system (5), each aperture system having slot apertures arranged circularly and concentrically around a longitudinal axis of the measuring cell (3), wherein the first inner aperture system (4) and the second outer aperture system (5) have different slot widths depending on the observed angle range of the scattered light, and the slot widths of the first inner aperture system (4) and the second outer aperture system (5) are the same for a given observed angle range; and
d) detecting scattered light (7) emanating from the second outer aperture system with at least two detectors (6) arranged circularly and concentrically around the measuring cell (3) which collect the light scattered on the sample within set, different angle ranges,
characterized in that the detectors are shielded from scattered light beams, which do not come within the respectively set angle ranges, and remissions by a first inner aperture system (4) and a second outer aperture system (5) which are formed and arranged circularly and concentrically around a longitudinal axis of the measuring cell (3).

9. The method according to claim 8, wherein
the cylindrical measuring cell (3) into which the liquid medium that contains the sample is introduced has a bore hole (8) along its axis and is formed from a translucent material,
the liquid medium that contains the sample is introduced into the bore hole (8) along the axis of the measuring cell (3), and
the sample located within the bore hole (8) of the measuring cell (3) is illuminated transversely to the axis of the measuring cell by a laser beam (2).

10. A method for measuring light scattered on a sample located within a liquid medium, comprising:
   (a) providing an apparatus having a laser (1), a cylindrical measuring cell (3), a first inner aperture system (4), a second outer aperture system (5) and at least two detectors (6), wherein:
   the detectors (6) are arranged outside of the second outer aperture system (5) so that the detectors (6) collect the light scattered on the sample within set, different angle ranges,
   characterized in that the first inner aperture system (4) and the second outer aperture system (5) are formed and arranged circularly and concentrically around a longitudinal axis of the measuring cell (3); and
   further characterized in that the first inner aperture system (4) and the second outer aperture system (5) are both formed as slot apertures, wherein the number of slots in the two aperture systems corresponds to the number of detectors (6), and each of the aperture systems additionally has an inlet opening (9) and an outlet opening (10) for the laser beam (2); and
   further characterized in that the first inner aperture system (4) and the second outer aperture system (5) have different slot widths depending on the observed angle range of the light scattered on the sample, wherein the slot widths of the first inner aperture system (4) and of the second outer aperture system (5) are the same for a given observed angle range of the light scattered on the sample; and
   b) introducing the liquid medium that contains the sample into the cylindrical measuring cell (3),
   c) using the laser, illuminating the sample located within the measuring cell (3) transversely to the direction of filling the liquid medium in the measuring cell or transversely to the flow direction of the liquid medium within the measuring cell (3), and
   d) using the detectors, detecting resulting scattered light beams (7).

11. The method according to claim 10, wherein the measurement of the light scattered on the sample is taken by means of a batch measurement or an online measurement.

12. The method according to claim 11, wherein the sample was separated before the measurement by means of a chromatographic or a quasi-chromatographic separating method into individual fractions each having a substantially uniform particle size and/or a substantially uniform molar mass.

13. The method according to claim 12, wherein the sample separation takes place by means of HPLC or Field-Flow Fractionation.

* * * * *